United States Patent [19]

Wolfenson et al.

[11] Patent Number: 4,668,188

[45] Date of Patent: May 26, 1987

[54] ORAL IMPRESSION TRAY FOR FORMING A MOUTHGUARD

[76] Inventors: Gilbert B. Wolfenson, 10 Troilus Dr., Old Bridge, N.J. 08857; Philip J. Dworetzky, 120 Doe View Rd., Pound Ridge, N.Y. 10576

[21] Appl. No.: 823,768

[22] Filed: Jan. 29, 1986

[51] Int. Cl.[4] .............................................. A61C 9/00
[52] U.S. Cl. ...................................................... 433/37
[58] Field of Search .................. 433/37, 6, 5; 128/136

[56] References Cited

U.S. PATENT DOCUMENTS

| | | | |
|---|---|---|---|
| 2,705,492 | 4/1955 | Chandler | 128/136 |
| 2,707,951 | 5/1955 | Schackelford | 128/136 |
| 3,207,153 | 9/1965 | Goldstein | 433/37 |
| 3,878,610 | 4/1975 | Coscina | 433/37 |

Primary Examiner—Robert Peshock
Attorney, Agent, or Firm—E. Lieberstein

[57] ABSTRACT

The oral impression tray is adapted for use by a non-professional in making a form fitted mouthguard of his or her own dentition and comprises a base of U-shaped configuration, an inner and outer wall projecting upright from the base for forming a trough into which impression material is removably inserted for forming the mouthguard and end stops integrally connecting the outer and inner wall. The end stops are located a predetermined distance posteriorly from the outer wall and extend upwardly a predetermined height to maintain a predetermined separation between the upper and lower teeth during centric occlusion.

12 Claims, 8 Drawing Figures

FIG. 7
FIG. 2
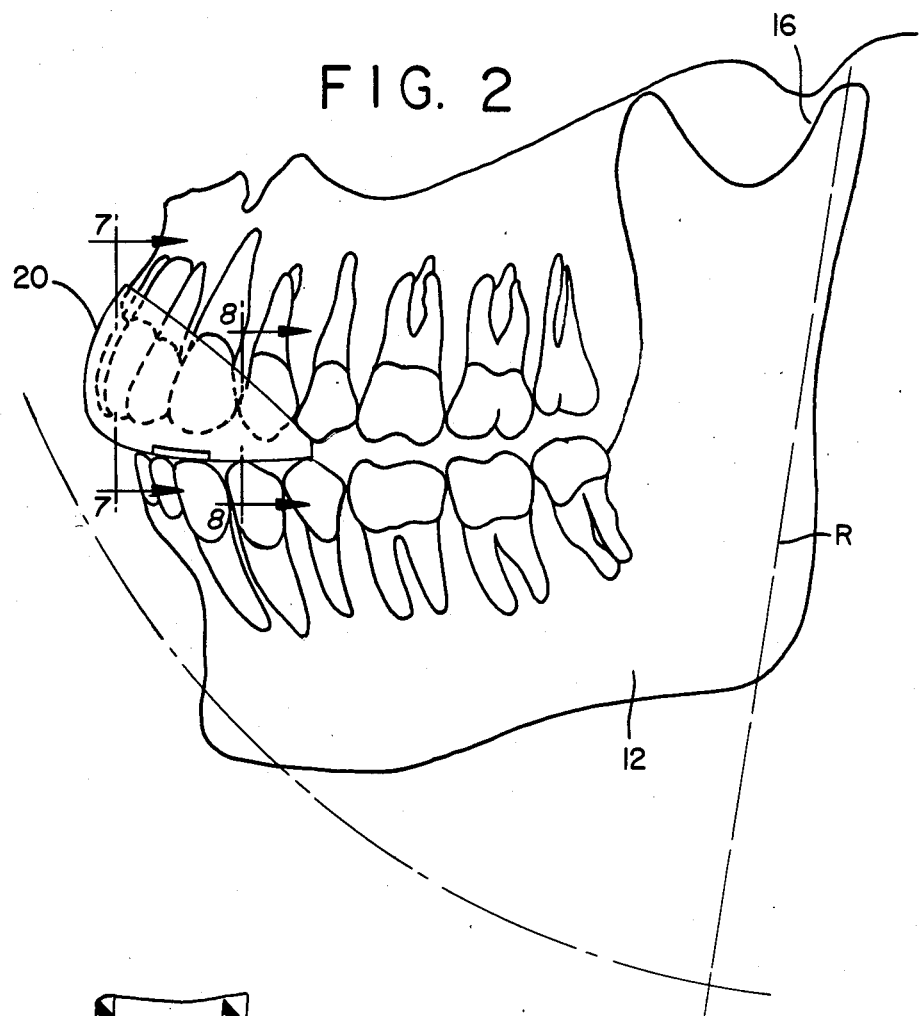
FIG. 8

ORAL IMPRESSION TRAY FOR FORMING A MOUTHGUARD

FIELD OF INVENTION

This invention relates to user formed mouthguards and to an oral impression tray for use by a consumer in making a form fitted mouthguard of his own dentition.

BACKGROUND OF INVENTION

Dentists customarily use an oral device referred to in the field of dentistry as a dental impression tray, to make a full impression of the maxillary and/or mandibular teeth or a partial impression of a selected quadrant of the upper or lower arch. To the dentist and dental technician, the impression of the dentition is necessary to reproduce the details of the teeth and to record and replicate their registration for the preparation of a dental restoration.

Mouth protecting oral devices have heretofore been developed for sports contact use to protect the teeth from injury. The prefabricated type mouthguard is a molded thermoplastic appliance designed to fit over the arch of a typical size mouth. Since the jaw and mouth of each individual varies in size and shape, the prefabricated type mouthguard is generally a poor fit and causes substantial physical discomfort to the user. Moreover, since a prefabricated type mouthguard does not conform to the impression of the user's teeth, the user must keep the jaws relatively closed to hold the mouthguard in place, which adds to the discomfort of the user. This also impairs breathing through the mouth. Accordingly, the user of a prefabricated type mouthguard will insert the mouthguard only when needed and will remove it as soon as possible. Such a mouthguard has also been proven to be a serious impediment to communication which further reduces its utility.

Attempts to provide a mouthguard with greater user comfort have been directed toward conforming the mouthguard to the dentition of the user. This type of mouthguard typically falls into one of two categories: (a) "custom made" by a dentist or other professional over a cast from an impression of the dentition using the same skill and knowledge in the preparation of an impression for a dental restoration or (b) formed by the user himself in conformity to his own dentition. The latter procedure is hereafter referred to as "user formed" and designates a procedure for making a mouthguard from a self-taken impression of one's own teeth although not strictly limited thereto.

Conventional user formed mouthguards are fabricated using a combination of an impression tray and impression material in which the tray acts both as a mold for the impression material following the same procedure used by a dentist in taking a dental impression and, in addition, as a reinforcing shell to reinforce and support the integrity of the molded impression material inside the shell for protecting the teeth. Although such a device has the potential for making a proper impression of the user's teeth, self application has proven to be extremely difficult and invariably results in the tray being seated poorly with unevenly distributed impression material causing discomfort and/or lack of protection. In addition, a mouthguard defined by the combination of an impression tray and impression material is inherently bulky and cumbersome. Moreover, the user will still experience difficulties in communicating with this device in the mouth similar to the prefabricated appliance.

The impression tray itself has heretofore been designed to function in a manner equivalent to a dental impression tray notwithstanding the fact that the dental impression tray is intended to be used by a skilled practitioner. When a conventional dental impression tray is used by an unskilled individual, and particularly if self applied, the user will invariably either bite through to the bottom of the tray or unevenly into the impression material or not deeply enough into the impression material. A skilled dentist knows how to position the tray and can control the degree of penetration to assure a uniform distribution of impression material around the dentition. Taking an accurate impression of the teeth should not be the critical criterion in making a mouthguard from impression material since the object of a mouthguard is not to replicate the teeth, but rather to conform the impression material to the teeth.

It has been discovered in accordance with the present invention that the impression material after it has cured can be separated from the tray and function itself as the mouthguard provided it is formed with an adequate amount of material around the dentition during the impression procedure. The impression tray of the present invention controls the distribution of impression material around the dentition and permits self application with reasonable accuracy and without any requisite skill.

It is therefore an object of the present invention to provide a disposable oral impression tray for use by a consumer in making a form fitted mouthguard of his own dentition.

It is another object of the present invention to provide an oral impression tray for use in combination with impression material for forming a user formed mouthguard from such impression material.

It is another object of the present invention to provide an oral impression tray for use in combination with impression material for forming a user formed mouthguard from such impression material.

It is yet a further object of the present invention to provide an oral impression tray for use in combination with impression material to produce a mouthguard from the impression material which does not significantly impede speaking by the user while in the mouth.

It is an even further object of the present invention to provide an oral impression tray for use in combination with impression material to produce a mouthguard from the impression material by self application with reasonable accuracy and without any requisite skill.

SUMMARY OF THE INVENTION

The oral impression tray of the present invention is designed to be used in combination with impression material to produce a form fitted mouthguard from the impression material by self application. A unique feature of the oral impression tray of the present invention, which distinguishes it from a conventional dental impression tray, is the incorporation of interference end stops posteriorly at a predetermined distance from the central incisors such that the impression is made without full centric occlusion between the maxilla and mandible. Instead, the degree of centric closure is precisely controlled by means of the interference end stops. This permits the user to readily fit the tray without experience and yet assure a uniform volume of impression material between the teeth and the tray particularly around the cusp regions of the teeth.

The oral impression tray of the present invention forms a mouthguard from impression material, which is removably inserted in the tray to form an impression of a section of teeth to be protected solely from the impression material upon withdrawal from the tray, with the tray comprising: a generally U-shaped trough having a substantially semi-circular arc to form a dental arch, an outer and inner wall projecting substantially upright from the base adjacent the lingual and labial surfaces of the section of teeth over which the tray is fitted, and end stops integrally connecting the outer and inner wall at a predetermined distance posteriorly from the central incisor teeth and extending upwardly from the base a predetermined height to maintain a predetermined degree of separation between the upper and lower teeth during centric occlusion.

The impression tray preferably includes additional means to facilitate self placement of the tray over the teeth to take an impression thereof with such means comprising a pair of tabular members which symmetrically extend outwardly from the planar base of the tray in substantial close proximity to the end stops respectively.

BRIEF DESCRIPTION OF THE DRAWINGS

Additional objects and advantages of the present invention will become apparent from the following detailed description of the invention when read in conjunction with the following drawings of which:

FIG. 2 is an isometric similar to FIG. 1 showing the impression tray of the present invention fitted with impression material and positioned in the mouth for making a mouthguard from the impression material of a section of the upper teeth;

FIG. 7 is a sectional view taken through the filled impression tray in FIG. 2 along the lines 7—7 thereof; and FIG. 8 is a sectional view taken through the filled impression tray in FIG. 2 along the lines 8—8 thereof;

DETAILED DESCRIPTION OF THE INVENTION

Figure 1:
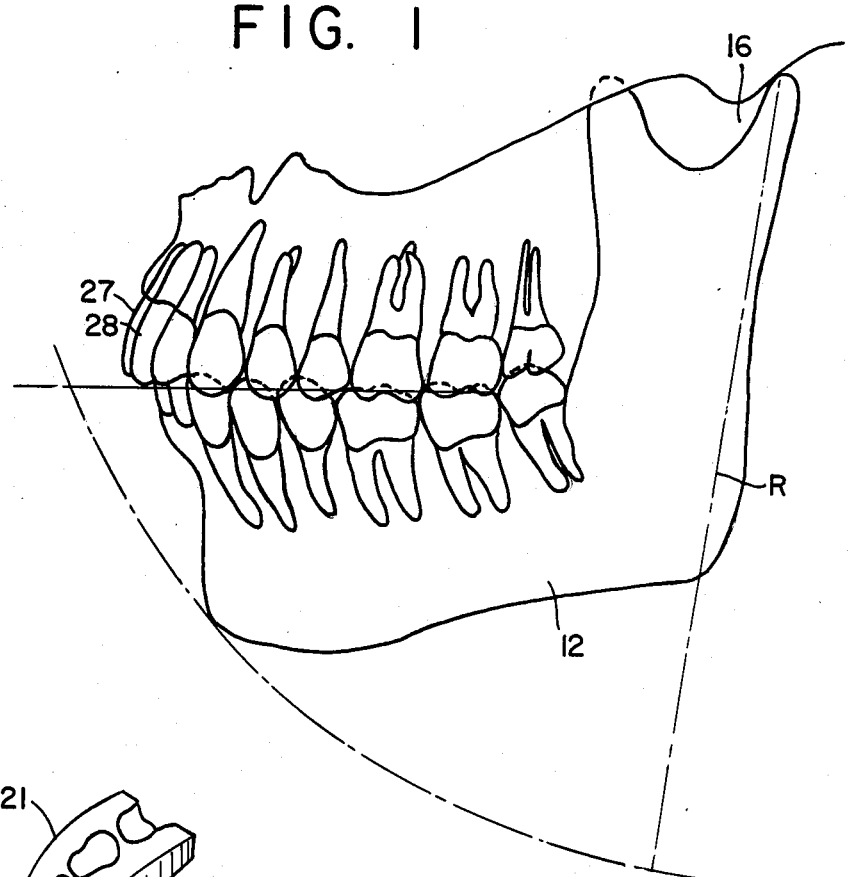
FIG. 1 is an isometric of the dentition of a human showing the relationship between the maxillary and mandibular jawbones during full centric closure of the upper and lower teeth.

FIG. 1 shows the relationship between the upper and lower teeth of the human dentition in full centric closure and maximum intercuspation between the teeth. The radius R represents the radius of rotation of the mandible 12 about an imaginary reference axis in the temporomadibular joint 16. The temporomandibular joint 16 permits substantial freedom of motion of the mandible 12 which moves both rotationally and translatory in opening and closing the jaws. As is known to those skilled in the art, the mandibular condyle rotates in its socket when the mouth is opened to no more than about 6 millimeters and any further opening of the mouth requires the condyle to slide. This movement permits the jaws to be substantially at rest both during full centric closure and when the mouth is slightly opened. Accordingly, balanced occlusion and comfort can be realized with a mouthguard which holds the upper and lower teeth slightly separated provided the mouthguard is sized properly and conforms to the teeth to which it has been molded.

Referring now to FIGS. 2–6 inclusive, showing an oral impression tray 20 for making a mouthguard 21 from curable mastic impression material inserted in the tray 20. The impression material used for making the mouthguard 21 is not a critical feature of the present invention but should possess certain desirable physical characteristics of flexibility, resiliency and tear resistance as is well known to those skilled in the art. While any resilient elastomeric impression material can be used in the practice of the invention, a particularly suitable material is a vinyl-terminated polysiloxane for use with a platinum catalyst. The preferred material should have a putty like consistency before curing so that it is easily molded. Upon curing the material should harden into a flexible body which is plastic and resilient and preferably characterized by a Shore A durometer rating of between 45 and 65 with 55 being optimum. A commercially available platinum-catalyzed vinyl end blocked polysiloxane composition which will satisfy the requisite requirements for the material composition of a mouthguard is sold by the Crown Delta Corporation in Yorktown Heights, New York.

The impression tray 20 is generally "U" shaped and has a planar base 22 which defines a semicircular arc of less than 180 degrees so that the tray 20 accurately spans only a predetermined section of teeth embracing the anterior teeth of the user but extending no further than the first molar. The tray 20 may be composed from any rigid polymeric material such as polypropylene. The tray 20 includes an inner wall 24 and an outer wall 26 which project from the planer base 22 relatively upright to conform to the lingual and buccal-labial surfaces of the teeth over which the tray 20 is fitted. The anterior teeth are longer in dimension than the molar teeth and gradually decrease in length from the central incisors 27 and 28 as shown in FIG. 1. Accordingly, the outer wall 26 of the tray 20 has a maximum height "H" slightly longer than the dimension of the central incisors 27 and 28 and gradually tapers down in height to approximate the gradual decrease in height from the front incisor teeth on the buccal surface to the bicuspids.

Figure 6:
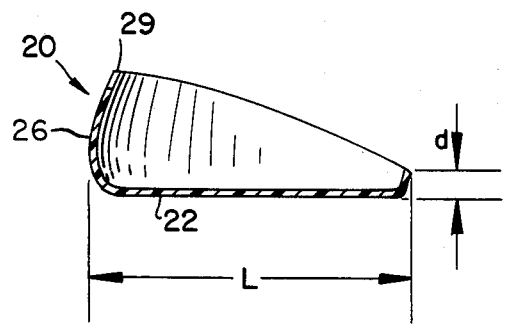
FIG. 6 is a sectional view of the impression tray of FIG. 4 taken along the lines 6—6 of FIG. 4.

The curvature of the outer wall 26 is crescent shaped to conform to the curvature of the anterior teeth buccolabially with a slight recurve as shown in FIGS. 2 and 6 such that the upper edge 29 of the outer wall 26 recedes backwardly in a curved path from the juncture with the base toward the gums to substantially permit contact with the gingiva tissue with minimal distortion of the lip. A "V" notch 30 at the symmetrical center of the outer wall 26 on the buccal surface allows clearance for the frenum and avoids impingement therewith. A score line 31 extending from the "V" notch 30 may also function as a centerline indicator for assisting the user in aligning the tray 20 with the midline of the teeth.

The curvature of the inner wall 24 conforms to the curvature of the teeth on the lingual surface. Accordingly, the inner wall 24 is inclined from the juncture 32 with the base 22 toward the outer edge 33 which should also extend slightly above the gingiva.

The width dimension W1 of the base of the tray 20 measured bucco-lingually from the centerline "V" notch 30 should be substantially narrower than the width dimension W2 of the base 22 measured labial-lingually. Stated otherwise, the planar base 22 between the inner wall 24 and the outer wall 26 should be narrow to conform to the incisal edge of the central incisor teeth 27 and 28 and widen substantially to conform to the occlusal surface of the posterior teeth.

The tray 20 further includes end stops 35 and 36 which integrally connect the inner and outer walls 24 and 26 respectively to define the other boundary of the tray. The end stops 35, 36 are located a predetermined distance "L" measured posteriorly from the "V" notch 30 on the outer wall 26. The location of the end stops 35, 36 relative to the central incosors, i.e., the distance "L", is critical to the present invention and must be selected such that the end stops 35 and 36 do not extend beyond the first molar of a mouthguard user independent of mouth size. Since the mouth size of each user will vary, with the greatest variation existing between adults and children, it is preferred that the dimension "L" be selected to correspond to the distance between the central incisor and first molar for a relatively small size mouth such that the mouthguard will extend only to, e.g., the first bicuspid for a very large size mouth. As an alternative, two or more size trays may be made available to fit, e.g., adults and children. There is no one critical length "L" which will provide universal application. However, a single length "L" of about 30 mm is believed satisfactory to fit the widest range of typical users.

The end stops 35 and 36 must also extend upwardly from the base 22 a predetermined height "d" in order to maintain a predetermined degree of separation between the upper and lower teeth in forming a mouthguard. The dimension "d" in conjunction with the distance "L" are critical to forming a mouthguard in accordance with the present invention. The height "d" should be between 2 to 5 mm in order to allow for a sufficient volume of metarial over the cusps of the teeth. This degree of spacing between the upper and lower teeth provides control over the degree of penetration into the impression material and still permits the jaws to be at rest as explained earlier notwithstanding the fact that the upper and lower teeth are held slightly apart. The end stops 35 and 36 should also be slightly inclined relative to the horizontal to form an inclined angle of, e.g., 15 degrees to limit the arc circumscribed by the tray 20 to less than 180 degrees.

The tray 20 is provided with tabular members 38 and 39 which can be gripped by the user to facilitate placement of the tray in the mouth. The tabs 38 and 39 are automatically dimensioned to accommodate the user's thumb and forefingers. The tabular members 38 and 39 extend from the planar base 22 symmetrically on each side of the tray 20 preferably for self placement by the user over the section of teeth upon which the tray is filled. Each tabular member 38 and 39 should extend outwardly, preferably in a plane parallel with the base 22, and in substantial close proximity to the corresponding end stops 35 and 36 respectively. The tabular members 38 and 39 also lie at an acute angle with respect to the horizontal.

Figure 3:
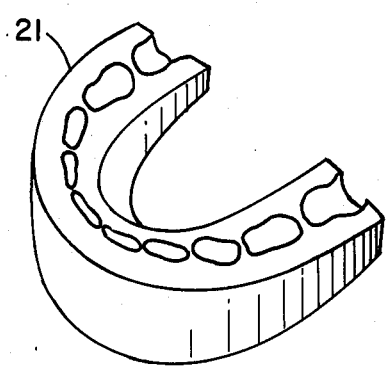
FIG. 3 is a plan view of the mouthguard made from the impression tray of the present invention.
Figure 4:
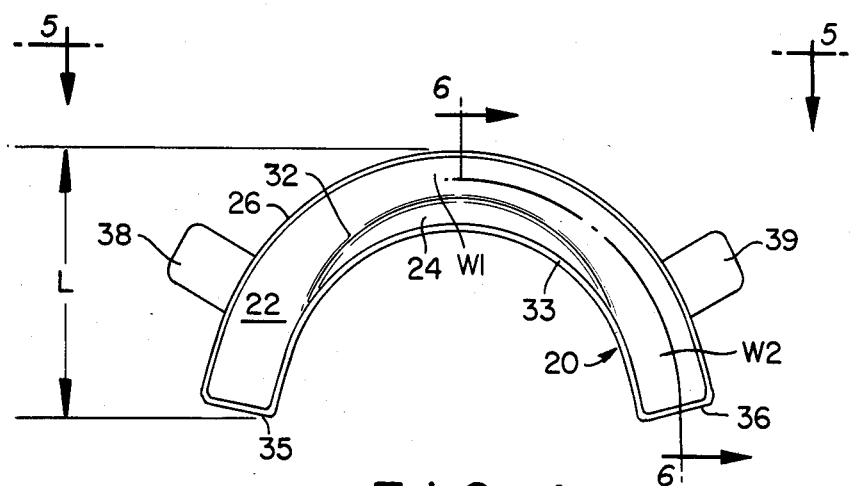
FIG. 4 is a top plan view of the impression tray of the present invention for forming the mouthguard in FIG. 3.
Figure 5:
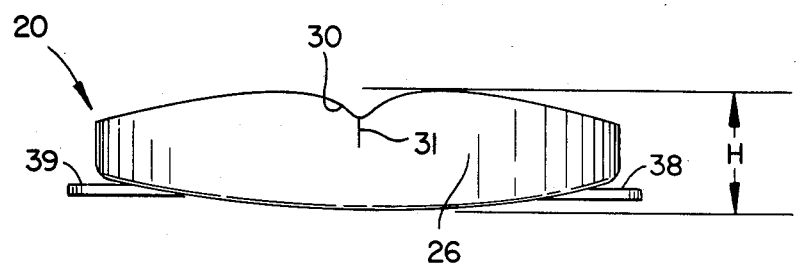
FIG. 5 is a front view of the impression tray of FIG. 4 taken along the lines 5—5 of FIG. 4.

The planar base 22 in combination with the inner and outer wall 24 and 26 respectively form a trough into which impression material is inserted for forming the mouthguard 21 as shown in FIG. 3. If a catalyst type impression material is used it is generally supplied in two parts one of which contains a putty like base and the other a putty like accelerator. Appropriate portions of base and accelerator are kneaded together to form a homogenous putty and inserted in the tray 20. As earlier indicated, a vinyl terminated polysiloxane with a platinum catalyst is preferred; particularly the material "Exp. 506" sold by the Crown Delta Corp. of Yorktown Heights, N.Y. The advantage of this material is that its putty like consistency is sticky and adheres to the tray 20 when taking the impression yet upon curing, is readily removed from the tray to function as the mouthguard 21.

What we claim is:

1. An oral impression tray for forming a mouthguard from impression material, adapted to be removably inserted into the tray to form an impression of a section of teeth to be protected by the impression material upon withdrawal from the tray, with the tray comprising; a planar base having a generally U-shaped configuration in a substantially semi-circular arc forming a less than a full dental arch, an inner and outer wall projecting upright from the base adjacent the lingual and buccal labial surfaces of said section of teeth for forming a trough about said section of teeth; and end stops integrally connecting said outer and inner wall for defining the outer boundary of said tray at a predetermined distance posteriorly from said outer wall at the juncture with the central incisor teeth and extending upwardly from said base a predetermined height to maintain a predetermined degree of separation between the upper and lower teeth during centric occlusion.

2. An oral impression tray as defined in claim 1 wherein said end stops extend a distance posteriorly from the central incisor teeth no further than the first molar independent of the size of the mouth of the mouthguard user.

3. An oral impression tray as defined in claim 2 further comprising a pair of tabular members which symmetrically extend outwardly from the planar base of the tray in substantial cose proximity to the end stops.

4. An oral impression tray as defined in claim 3 wherein said tabular members lie in plane substantially parallel to the plane of the base and at an acute angle with the horizontal.

5. An oral impression tray as defined in claims 3 or 4 wherein said outer wall has a crescent shape configuration conforming to the curvature of the anterior teeth with a "V" notch at the symmetrical center thereof to allow clearance for the frenum.

6. An oral impression tray as defined in claim 5 wherein said outer wall has a slight recurve bucco-labially receding in a curved path from the juncture with said planar base to substantially permit contact with the gingiva tissue with minimal distortion of the lip.

7. An oral impression tray as defined in claim 6 further comprising a score line extending from the "V" notch as a centerline indicator of the tray.

8. An oral impression tray as defined in claim 6 wherein said planar base has a wider width bucco-lingually than its width labio-lingually.

9. An oral impression tray as defined in claim 8 wherein said tray is composed of a polymeric material.

10. An oral impression tray as defined in claim 9 wherein said end stops are inclined relative to the horizontal to limit the arc circumscribed by the tray to less than 180 degrees.

11. An oral impression tray as defined in claim 10 wherein said end stops are between 2–5 mm in height.

12. An oral impression tray as defined in claim 11 wherein said end stops extend about 30 mm from said "V" notch on the outer wall.

* * * * *